US007842658B2

(12) United States Patent
Guckenbiehl et al.

(10) Patent No.: US 7,842,658 B2
(45) Date of Patent: Nov. 30, 2010

(54) DETERGENT OR CLEANING AGENT COMPRISING POLYSACCHARIDE

(75) Inventors: Bernhard Guckenbiehl, Köln (DE); Sören Hölsken, Düsseldorf (DE); Carine Wattebled, Düsseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/613,095

(22) Filed: Nov. 5, 2009

(65) Prior Publication Data

US 2010/0105600 A1 Apr. 29, 2010

Related U.S. Application Data

(63) Continuation of application No. PCT/EP2008/054212, filed on Apr. 8, 2008.

(30) Foreign Application Priority Data

May 7, 2007 (DE) ....................... 10 2007 021 793

(51) Int. Cl.
*C11D 3/22* (2006.01)
*C11D 1/00* (2006.01)
*A61K 8/73* (2006.01)

(52) U.S. Cl. ....................... 510/471; 510/326; 510/405; 510/421; 510/426; 510/438; 510/451; 510/473; 424/488; 424/493; 424/70.13

(58) Field of Classification Search ................. 510/326, 510/405, 421, 426, 438, 451, 471, 473; 424/488, 424/493, 70.13
See application file for complete search history.

(56) References Cited

U.S. PATENT DOCUMENTS 5,259,984 A 11/1993 Hull

FOREIGN PATENT DOCUMENTS

| | | | |
|---|---|---|---|
| EP | 0054325 | B1 | 4/1984 |
| WO | 2004005444 | A1 | 1/2004 |
| WO | WO 2004/005444 | * | 1/2004 |

* cited by examiner

*Primary Examiner*—Brian P Mruk
(74) *Attorney, Agent, or Firm*—David P. LeCroy

(57) ABSTRACT

The invention describes a stable and transparent liquid washing agent or liquid cleaning agent having a graying-inhibiting polysaccharide that has a particle size smaller than 100 nm. The invention also relates to the use of the liquid washing agent or liquid cleaning agent, and to a method for the manufacture thereof.

9 Claims, No Drawings

DETERGENT OR CLEANING AGENT COMPRISING POLYSACCHARIDE

CROSS REFERENCE TO RELATED APPLICATIONS

The present application is a continuation of International Application No. PCT/EP2008/054212 filed 8 Apr. 2008, which claims the benefit of German Patent Application No. 10 2007 021 793.7 A1 filed 7 May 2007.

The present invention relates to liquid washing or cleaning agents containing surfactant(s), a polysaccharide, and other typical ingredients found in washing or cleaning agents. The invention also relates to the use of the washing or cleaning agent, and to a method for the manufacture thereof.

Washing or cleaning agents often contain one or more additives in order to increase their washing or cleaning performance. For example, in order to prevent redeposition of finely distributed dirt that has previously been removed, washing agents may contain so-called graying inhibitors such as carboxymethyl cellulose.

EP 0054325 A1, for example, describes a washing agent having carboxymethyl cellulose as a graying inhibitor.

In recent years, liquid washing or cleaning agents have increasingly been offered in transparent bottles. Because of its low solubility in liquid washing or cleaning agents, clouding can occur when carboxymethyl cellulose is incorporated into liquid washing or cleaning agents. This results in a product having little aesthetic appeal, especially when it is offered in a transparent bottle.

A further problem is that stable dispersions of carboxymethyl cellulose in the matrix of a washing or cleaning agent are very difficult to obtain.

It is therefore an object of the invention to make available a liquid washing or cleaning agent having a polysaccharide as a graying inhibitor and that is stable and aesthetically appealing.

This object is achieved by a liquid washing or cleaning agent containing one or more surfactants as well as other ingredients typically found in washing or cleaning agents.

In this respect, the agent includes a graying-inhibiting polysaccharide having a particle size smaller than 100 nm. Particularly preferably, the agent comprises a graying-inhibiting polysaccharide having a particle size smaller than 50 nm.

It has been found that graying-inhibiting polysaccharides having a particle size smaller than 100 nm can be incorporated in stable fashion into a liquid washing or cleaning agent matrix. In addition, the resulting washing or cleaning agent dispersions are homogeneous and transparent. The washing or cleaning agent according to the present invention furthermore exhibits considerably better graying inhibition than a washing or cleaning agent having a graying-inhibiting polysaccharide of a larger particle diameter.

It is preferred that the quantity of graying-inhibiting polysaccharide be from 0.001 to 10 wt %, preferably 0.01 to 8 wt %.

It is advantageous if the graying-inhibiting polysaccharide is chosen from carboxymethyl cellulose (CMC), ethersulfonic acid salts of starch, ethersulfonic acid salts of cellulose, acid sulfuric acid ester salts of cellulose, acid sulfuric acid ester salts of starch, methyl cellulose, ethyl cellulose, hydroxyethyl cellulose, hydroxypropyl cellulose, methylhydroxyethyl cellulose, methylcarboxymethyl cellulose, ethylhydroxyethyl cellulose, and mixtures thereof. Preferably, the polysaccharide is carboxymethyl cellulose, and in particular, sodium carboxymethyl cellulose.

These preferred graying-inhibiting polysaccharides in preferred quantities result in washing or cleaning agents having a particularly good anti-graying effect.

Polysaccharides having a particle size smaller than 100 nm have been obtained by applying a mechanical comminution method to larger polysaccharide particles. Graying-inhibiting polysaccharides having a particle size smaller than 100 nm can, in this manner, be manufactured easily and quickly from commercially obtainable graying-inhibiting polysaccharides.

The invention further relates to the use of washing or cleaning agents according to the present invention for washing and/or cleaning textile fabrics.

In a further aspect, the invention relates to a method for manufacturing a liquid washing or cleaning agent containing one or more surfactants, a graying-inhibiting polysaccharide having a particle size smaller than 100 nm, and other ingredients typically found in washing or cleaning agents, wherein a) polysaccharide particles having a particle size larger than or equal to 100 nm are processed, by means of a mechanical comminution method, into polysaccharide particles having a particle diameter smaller than 100 nm; and
b) the polysaccharide particles having a particle diameter smaller than 100 nm are mixed with the surfactants and with the other constituents of the washing or cleaning agent.

For cost reasons and from the standpoint of simplicity, it is preferred that the milling method used is a mechanical comminution method.

Washing or cleaning agents according to the invention contain a graying-inhibiting polysaccharide. The graying-inhibiting polysaccharide is preferably carboxymethyl cellulose (CMC), an ethersulfonic acid salt of starch, an ethersulfonic acid salt of cellulose, an acid sulfuric acid ester salt of cellulose, an acid sulfuric acid ester salt of starch, methyl cellulose, ethyl cellulose, hydroxyethyl cellulose, hydroxypropyl cellulose, methylhydroxyethyl cellulose, methylcarboxymethyl cellulose, ethylhydroxyethyl cellulose, or a mixture of such graying-inhibiting polysaccharides. Very preferably, the polysaccharide is carboxymethyl cellulose, and in particular, sodium carboxymethyl cellulose.

Graying-inhibiting polysaccharides according to the invention have a particle diameter smaller than 100 nm, preferably smaller than 50 nm. These small particle diameters ensure that a stable dispersion of the washing or cleaning agent containing the graying-inhibiting polysaccharide is obtained. In addition, these small particle diameters ensure that the washing or cleaning agents are not cloudy, but instead transparent.

In order to manufacture the polysaccharide particles having a particle diameter smaller than 100 nm, commercially obtainable polysaccharide particles having a particle diameter larger than 100 nm are processed by a mechanical comminution method into particles having the desired particle size. Commercially obtainable polysaccharide particles having a particle diameter larger than 100 nm are preferably milled into particles having a particle diameter smaller than 100 nm.

Particle diameter of the graying-inhibiting polysaccharide can be determined by conventional methods, for example, with the aid of a condensation particle counter or a laser particle sizer.

The washing or cleaning agent contains one or more surfactants in addition to the graying-inhibiting polysaccharide. In this respect, anionic, nonionic, zwitterionic, and/or amphoteric surfactants can be used. Mixtures of anionic and nonionic surfactants are preferred from an applications/engineering point of view. Total surfactant content of the liquid washing or cleaning agent is preferably below 60 wt %, and particularly preferably below 45 wt %, based on weight of the entire liquid washing or cleaning agent.

When nonionic surfactants are used, they are preferably alkoxylated and advantageously ethoxylated. In particular, primary alcohols having 8 to 18 carbon atoms and an average of 1 to 12 mol ethylene oxide (EO) units per mol of alcohol, in which the alcohol residue can be linear or preferably methyl-branched in the 2-position, or can contain mixed linear and methyl-branched residues, such as those that are usually present in oxo-alcohol residues, are preferred. Particularly preferred are alcohol ethoxylates having linear residues made up of alcohols of natural origin having 12 to 18 carbon atoms (e.g. from coconut, palm, tallow, or oleyl alcohol) and an average of 2 to 8 EO units per mol of alcohol. Preferred ethoxylated alcohols include, for example, $C_{12-14}$ alcohols with 3 EO, 4 EO, or 7 EO units, $C_{9-11}$ alcohols with 7 EO units, $C_{13-15}$ alcohols with 3 EO, 5 EO, 7 EO, or 8 EO units, $C_{12-18}$ alcohols with 3 EO, 5 EO, or 7 EO units, and mixtures thereof, such as mixtures of $C_{12-14}$ alcohol with 3 EO units and $C_{12-18}$ alcohol with 7 EO units. The degrees of ethoxylation indicated represent statistical averages which can correspond to an integral or a fractional number for a specific product. Preferred alcohol ethoxylates exhibit a restricted distribution of homologs (narrow range ethoxylates, NRE). In addition to these nonionic surfactants, fatty alcohols with more than 12 EO units can also be used. Examples of these are tallow fatty alcohol with 14 EO, 25 EO, 30 EO, or 40 EO units. Nonionic surfactants that contain EO and PO groups together in the molecule are also usable according to the present invention. Block copolymers having EO-PO block units or PO-EO block units, but also EO-PO-EO copolymers or PO-EO-PO copolymers, can be used in this context. Also usable are mixed alkoxylated nonionic surfactants wherein the EO and PO units are distributed statistically rather than in block fashion. Such products are obtainable by the simultaneous action of ethylene oxide and propylene oxide on fatty alcohols.

Also usable as nonionic surfactants are alkyl glycosides of the general formula $RO(G)_x$, wherein R denotes a primary straight-chain or methyl-branched (particularly methyl-branched in the 2-position) aliphatic residue having 8 to 22 carbon atoms, and by preference 12 to 18 carbon atoms; and G denotes a glycose unit having 5 or 6 carbon atoms, preferably glucose. The degree of oligomerization x, which indicates the distribution of monoglycosides and oligoglycosides, is any number between 1 and 10; by preference, x is between 1.2 and 1.4. Alkyl glycosides are known mild surfactants.

Another class of preferred nonionic surfactants, which can be formulated either as the only nonionic surfactant or in combination with other nonionic surfactants, are alkoxylated, preferably ethoxylated or ethoxylated and propoxylated, fatty acid alkyl esters, by preference having 1 to 4 carbon atoms in the alkyl chain, in particular fatty acid methyl esters.

Nonionic surfactants of the amine oxide type, for example N-cocalkyl-N,N-dimethylamine oxide and N-tallowalkyl-N,N-dihydroxyethylamine oxide, and the fatty acid alkanolamides, are also suitable for use. The quantity of these nonionic surfactants is preferably no more than that of the ethoxylated fatty alcohols, in particular, no more than half thereof.

Further suitable surfactants are polyhydroxy fatty acid amides of formula (I)

(I)

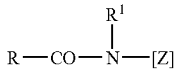

wherein R—CO represents an aliphatic acyl residue having 6 to 22 carbon atoms; $R^1$ represents hydrogen, an alkyl or a hydroxyalkyl residue having 1 to 4 carbon atoms; and [Z] represents a linear or branched polyhydroxyalkyl residue having 3 to 10 carbon atoms and 3 to 10 hydroxyl groups. Polyhydroxy fatty acid amides are known substances that can be obtained by reductive amination of a reducing sugar with ammonia, alkylamine, or alkanolamine, and subsequent acylation with a fatty acid, a fatty acid alkyl ester, or a fatty acid chloride.

Also belonging to the group of the polyhydroxy fatty acid amides are compounds of formula (II)

(II)

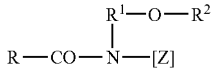

wherein R represents a linear or branched alkyl or alkenyl residue having 7 to 12 carbon atoms; $R^1$ represents a linear, branched, or cyclic alkyl residue or an aryl residue having 2 to 8 carbon atoms; and $R^2$ represents a linear, branched, or cyclic alkyl residue or an aryl residue or an oxyalkyl residue having 1 to 8 carbon atoms ($C_{1-4}$ alkyl or phenyl residues being preferred); and [Z] represents a linear polyhydroxyalkyl residue whose alkyl chain is substituted with at least two hydroxyl groups, or alkoxylated, preferably ethoxylated or propoxylated, derivatives of that residue.

[Z] is preferably obtained by reductive amination of a sugar, for example glucose, fructose, maltose, lactose, galactose, mannose, or xylose. The N-alkoxy- or N-aryloxy-substituted compounds can then be converted into the desired polyhydroxy fatty acid amides by reaction with fatty acid methyl esters in the presence of an alkoxide as catalyst.

The concentration of nonionic surfactants in the washing or cleaning agents is preferably 5 to 30 wt %, more preferably 7 to 20 wt %, and most preferably 9 to 15 wt %, each based on the weight of the entire washing or cleaning agent.

In addition to nonionic surfactants, the washing or cleaning agent can also contain anionic surfactants. Anionic surfactants that can be used are, for example, those of the sulfonate and sulfate types. Possible surfactants of the sulfonate type are, by preference, $C_{9-13}$ alkylbenzenesulfonates, olefinsulfonates (i.e., mixtures of alkene- and hydroxyalkanesulfonates), and disulfonates, such as those obtained from $C_{12-18}$ monoolefins having an end-located or internal double bond, by sulfonation with gaseous sulfur trioxide and subsequent alkaline or acid hydrolysis of the sulfonation products. Also suitable are alkanesulfonates obtained from $C_{12-18}$ alkanes, for example, by sulfochlorination or sulfoxidation with subsequent hydrolysis and neutralization. Esters of α-sulfo fatty acids (estersulfonates, e.g., the α-sulfonated methyl esters of hydrogenated coconut, palm kernel, or tallow fatty acids) are likewise suitable.

Further suitable anionic surfactants are sulfonated fatty acid glycerol esters. "Fatty acid glycerol esters" are understood to refer to mono-, di- and triesters and mixtures thereof obtained during production of a monoglycerol with 1 to 3 mol fatty acid by esterification, or upon transesterification of triglycerides with 0.3 to 2 mol glycerol. Preferred sulfonated fatty acid glycerol esters are the sulfonation products of saturated fatty acids having 6 to 22 carbon atoms, for example, hexanoic acid, octanoic acid, decanoic acid, myristic acid, lauric acid, palmitic acid, stearic acid, or behenic acid.

Preferred alk(en)yl sulfates are the alkali, and in particular sodium, salts of sulfuric acid semi-esters of $C_{12}$-$C_{18}$ fatty alcohols, for example from coconut fatty alcohol, tallow fatty alcohol, lauryl, myristyl, cetyl, or stearyl alcohol, or of the $C_{10}$-$C_{20}$ oxo-alcohols, and those semi-esters of secondary alcohols of those chain lengths. Additionally preferred are alk(en)yl sulfates of the aforesaid chain length that contain a synthetic straight-chain alkyl residue produced on a petrochemical basis, which possess a breakdown behavior analogous to those appropriate compounds based on fat-chemistry raw materials. For purposes of washing technology, the $C_{12}$-$C_{16}$ alkyl sulfates and $C_{12}$-$C_{15}$ alkyl sulfates, as well as $C_{14}$-$C_{15}$ alkyl sulfates, are preferred. 2,3-Alkyl sulfates that can be obtained, for example, as commercial products of the Shell Oil Company under the tradename DAN®, are also suitable anionic surfactants.

The sulfuric acid monoesters of straight-chain or branched $C_{7-21}$ alcohols ethoxylated with 1 to 6 mol ethylene oxide, such as 2-methyl-branched $C_{9-11}$ alcohols having an average of 3.5 mol ethylene oxide (EO) units or $C_{12-18}$ fatty alcohols having 1 to 4 EO units are also suitable. It is preferred that washing or cleaning agents according to the present invention contain 0.01 to 5 wt %, preferably 0.5 to 3 wt %, and most preferably 1.5 to 2.5 wt %, of an ethoxylated fatty alcohol sulfate.

Other suitable anionic surfactants include the salts of alkylsulfosuccinic acid, also referred to as sulfosuccinates or sulfosuccinic acid esters and represent the monoesters and/or diesters of sulfosuccinic acid with alcohols, preferably fatty alcohols, and most preferably ethoxylated fatty alcohols. Preferred sulfosuccinates contain $C_{8-18}$ fatty alcohol residues or mixtures thereof. Particularly preferred sulfosuccinates contain a fatty alcohol residue derived from ethoxylated fatty alcohols that, considered per se, represent nonionic surfactants. Sulfosuccinates whose fatty alcohol residues derive from ethoxylated fatty alcohols having a restricted homolog distribution are particularly preferred. It is likewise also possible to use alk(en)ylsuccinic acid having 8 to 18 carbon atoms in the alk(en)yl chain or salts thereof.

Particularly preferred anionic surfactants are soaps. Saturated and unsaturated fatty acid soaps, such as salts of lauric acid, myristic acid, palmitic acid, stearic acid, (hydrogenated) erucic acid, and behenic acid, are suitable as are soap mixtures derived from natural fatty acids (e.g., coconut, palm-kernel, olive-oil, or tallow fatty acids).

Anionic surfactants including soaps can be present in the form of their sodium, potassium, or ammonium salts. Anionic surfactants are preferably present in the form of their sodium salts.

The concentration of anionic surfactants in a washing or cleaning agent can be 0.1 to 30 wt %, based on the weight of the entire washing or cleaning agent.

In addition to the graying-inhibiting polysaccharide and the surfactant(s), the washing or cleaning agents can contain other ingredients that further improve the aesthetic and/or applications/engineering properties of the washing or cleaning agent. In the context of the present invention, the washing or cleaning agent preferably contains one or more substances chosen from detergency builders, bleaching agents, enzymes, electrolytes, nonaqueous solvents, pH adjusting agents, perfumes, perfume carriers, fluorescing agents, dyes, hydrotopes, foam inhibitors, silicone oils, anti-redeposition agents, further graying inhibitors, shrinkage preventers, wrinkle protection agents, color transfer inhibitors, antimicrobial active substances, germicides, fungicides, antioxidants, preservatives, corrosion inhibitors, antistatic agents, bittering agents, ironing adjuvants, proofing and impregnation agents, swelling and anti-slip agents, neutral filler salts, softening compounds, and UV absorbers.

Silicates, aluminum silicates (in particular zeolites), carbonates, salts of organic di- and polycarboxylic acids, and mixtures of these substances, are suitable detergency builders that can be included in the washing or cleaning agent.

Suitable crystalline, sheet-form sodium silicates possess the general formula $NaMSi_xO_{2x+1}.yH_2O$, where M represents sodium or hydrogen, x is a number from 1.9 to 4, and y is a number from 0 to 20, and preferred values for x are 2, 3, or 4. Preferred crystalline sheet silicates of the formula indicated above are those in which M denotes sodium and x assumes the value 2 or 3. Both β- and δ-sodium disilicates $Na_2Si_2O_5.yH_2O$ are particularly preferred.

Also suitable are amorphous sodium silicates having a $Na_2O:SiO_2$ modulus from 1:2 to 1:3.3, preferably from 1:2 to 1:2.8, and most preferably from 1:2 to 1:2.6, which are dissolution-delayed and exhibit secondary washing properties. The dissolution delay as compared with conventional amorphous sodium silicates can be brought about in various ways, for example, by surface treatment, compounding, compacting/densification, or overdrying. In the context of this invention, the term "amorphous" is also understood to mean "X-amorphous". In other words, in X-ray diffraction experiments the silicates do not yield sharp X-ray reflections typical of crystalline substances, but at most one or more maxima in the scattered X radiation that have a width of several degree units of the diffraction angle. Particularly good builder properties can, however, be very easily obtained even if the silicate particles yield blurred or even sharp diffraction maxima in electron beam diffraction experiments. This may be interpreted to mean that the products comprise microcrystalline regions 10 to several hundred nm in size, values of up to a maximum of 50 nm, and in particular a maximum of 20 nm, being preferred. Densified/compacted amorphous silicates, compounded amorphous silicates, and overdried X-amorphous silicates are particularly preferred.

Finely crystalline synthetic zeolite containing bound water that is used is preferably zeolite. A and/or zeolite P. Zeolite MAP® (commercial product of the Crosfield Co.) is particularly preferred as zeolite P. Also suitable, however, are zeolite X as well as mixtures of A, X, and/or P. Also commercially available and preferably usable in the context of the present invention is, for example, a co-crystal of zeolite X and zeolite A (approx. 80 wt % zeolite X) that is marketed by the Sasol company under the trade name VEGOBOND AX® and can be described by the formula $$nNa_2O.(1-n)K_2O.Al_2O_3.(2-2.5)SiO_2.(3.5-5.5)H_2O$$
$$n=0.90-1.0$$

The zeolite can be used as a spray-dried powder or also as an undried stabilized suspension still moist as manufactured. In the event the zeolite is used as a suspension, it can contain small additions of nonionic surfactants as stabilizers, for example, 1 to 3 wt %, based on weight of the zeolite, of ethoxylated $C_{12}$-$C_{18}$ fatty alcohols having 2 to 5 ethylene oxide groups, $C_{12}$-$C_{14}$ fatty alcohols having 4 to 5 ethylene oxide groups, or ethoxylated isotridecanols. Suitable zeolites exhibit an average particle size of less than 10 μm (volume distribution; measurement method: Coulter Counter), and preferably contain 18 to 22 wt %, more preferably 20 to 22 wt %, bound water.

Use of phosphates as builder substances is also possible, provided such use is environmentally acceptable. Sodium salts of orthophosphates, pyrophosphates, and in particular, tripolyphosphates, are particularly suitable.

Organic builder substances that can be present in the washing or cleaning agent include, for example, polycarboxylic acids in the form of their sodium salts, "polycarboxylic acids" being understood as those carboxylic acids that carry more than one acid function. These are, for example, citric acid, adipic acid, succinic acid, glutaric acid, malic acid, tartaric acid, maleic acid, fumaric acid, sugar acids, aminocarboxylic acids, nitrilotriacetic acid (NTA), methylglycinediacetic acid (MGDA) and their descendants, as well as mixtures thereof. Preferred salts are the salts of the polycarboxylic acids such as citric acid, adipic acid, succinic acid, glutaric acid, tartaric acid, sugar acids, and mixtures thereof.

Acids per se can also be used. Acids typically possess not only a builder effect but also the benefit of an acidifying component, thereby providing a lower and milder pH for washing or cleaning agents. Suitable acids include citric acid, succinic acid, glutaric acid, adipic acid, gluconic acid, and any mixtures thereof. Further known pH regulators include sodium hydrogencarbonate and sodium hydrogensulfate.

Polymeric polycarboxylates are also suitable as builders. These include alkali metal salts of polyacrylic acid or of polymethacrylic acid, such as those having a relative molecular weight from 500 to 70,000 g/mol.

Molar weights indicated for the polymeric polycarboxylates refer to weight-averaged molar weights $M_w$ of the respective acid form determined by gel permeation chromatography (GPC), a UV detector having been used. The measurement was performed against an external polyacrylic acid standard that yields realistic molecular weight values due to its structural affinity with the polymers being investigated. These indications deviate considerably from molecular weight indications in which polystyrene sulfonic acids are used as a standard. Molar weights measured against polystyrene sulfonic acids are usually much higher than molar weights indicated in this document.

Suitable polymers include polyacrylates having a molecular weight from 2000 to 20,000 g/mol. Of this group, short-chain polyacrylates having molar weights from 2000 to 10,000 g/ml, particularly from 3000 to 5000 g/mol, are preferred because of their superior solubility.

Suitable polymers also include substances comprised partly or entirely of units of vinyl alcohol or derivatives thereof.

Copolymeric polycarboxylates, in particular, those of acrylic acid with methacrylic acid and of acrylic acid or methacrylic acid with maleic acid, are also suitable. Copolymers of acrylic acid with maleic acid comprising 50 to 90 wt % acrylic acid and 50 to 10 wt % maleic acid have proven particularly suitable. Their relative molecular weight, based on free acids, is generally 2000 to 70,000 g/mol, preferably 20,000 to 50,000 g/mol, and most preferably 30,000 to 40,000 g/mol. The (co)polymeric polycarboxylates can be used either as an aqueous solution or as a powder.

To improve water solubility, the polymers can also contain allylsulfonic acids such as allyl oxybenzene sulfonic acid and methallyl sulfonic acid as monomers.

Also preferred are biodegradable polymers made up of more than two different monomer units, for example, those that contain as monomers, salts of acrylic acid and maleic acid, as well as vinyl alcohol or vinyl alcohol derivatives, or, as monomers, salts of acrylic acid and 2-alkyallylsulfonic acid, as well as sugar derivatives.

Further preferred copolymers include those that comprise acrolein and acrylic acid/acrylic acid salts, or acrolein and vinyl acetate, as monomers.

Detergency builders also include polymeric amino dicarboxylic acids, salts thereof, or precursor substances thereof. Polyaspartic acids and salts and derivatives thereof, which also have a bleach-stabilizing action in addition to builder properties, are particularly preferred.

Further suitable builder substances include polyacetals, obtainable by reacting dialdehydes with polyolcarboxylic acids having 5 to 7 carbon atoms and at least three hydroxyl groups. Preferred polyacetals are obtained from dialdehydes such as glyoxal, glutaraldehyde, terephthalaldehyde and mixtures thereof, and from polyolcarboxylic acids such as gluconic acid and/or glucoheptonic acid.

Further suitable organic builder substances include dextrins such as oligomers or polymers of carbohydrates, obtainable by partial hydrolysis of starches. The hydrolysis can be carried out in accordance with usual methods such as acid- or enzyme-catalysis. These hydrolysis products can have average molar weights in the range from 400 to 500,000 g/mol. Polysaccharides having a dextrose equivalent (DE) in the range from 0.5 to 40, in particular from 2 to 30, are preferred. (DE is a common indicator of the reducing effect of a polysaccharide as compared with dextrose, which possesses a DE of 100.) Maltodextrins having a DE between 3 and 20 and dry glucose syrups having a DE between 20 and 37, as well as so-called yellow and white dextrins having higher molar weights in the range from 2000 to 30,000 g/mol, are usable.

Oxidized derivatives of such dextrins are their reaction products with oxidizing agents that are capable of oxidizing at least one alcohol function of the saccharide ring to the carboxylic acid function. An oxidized oligosaccharide is likewise suitable. A product oxidized at $C_6$ of the saccharide ring can be particularly advantageous.

Oxydisuccinates and other derivatives of disuccinates, by preference ethylenediamine disuccinate, are also additional suitable cobuilders. Ethylenediamine-N,N'-disuccinate (EDDS) is preferably used here, in the form of its sodium or magnesium salts. Also preferred in this context are glycerol disuccinates and glycerol trisuccinates.

Other usable organic detergency builders are, for example, acetylated hydroxycarboxylic acids and their salts, which can optionally also be present in lactone form and which contain at least 4 carbon atoms and at least one hydroxy group, as well as a maximum of two acid groups.

For aesthetic reasons, however, soluble organic detergency builders such as, for example, citric acid are preferably used in the washing or cleaning agents.

Among the compounds that serve as bleaching agents and yield $H_2O_2$ in water, sodium perborate tetrahydrate and sodium perborate monohydrate are particularly important. Other usable bleaching agents are, for example, sodium percarbonate, peroxypyrophosphates, citrate perhydrates, and peracid salts or peracids that yield $H_2O_2$, such as perbenzoates, peroxophthalates, diperazelaic acid, diperdodecanedioic acid, 4-phthalimidoperoxobutanoic acid, 5-phthalimidoperoxopentanoic acid, 6-phthalimidoperoxohexanoic acid, 7-phthalimidoperoxoheptanoic acid, N,N'-terephthaloyldi-6-aminoperoxohexanoic acid, and mixtures thereof. The phthalimidoperoxoalkanoic acids, in particular 6-phthalimidoperoxohexanoic acid (PAP), are among the preferred peracids. It may be preferred for the bleaching agent to comprise a casing that dissolves only in the actual washing process and then releases the bleaching agent.

The quantity of bleaching agent is by preference between 0.5 and 25 wt %, based on the entire washing or cleaning agent.

In order to achieve an improved bleaching effect when washing at temperatures of 60° C. and below, bleach activators can be incorporated into the washing and cleaning agents. Compounds that yield aliphatic peroxycarboxylic acids under perhydrolysis conditions can be used as bleach activators. Multiply acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoylsuccinimide (NOSI), acylated phenolsulfonates, in particular n-nonanoyl- or isononanoyloxybenzene-sulfonate (n- or iso-NOBS), carboxylic acid anhydrides, in particular phthalic acid anhydride, acylated polyvalent alcohols, in particular triacetin, ethylene glycol diacetate, and 2,5-diacetoxy-2,5-dihydrofuran, are preferred.

In addition to or instead of the conventional bleach activators, so-called bleach catalysts can also be used. These substances are bleach-enhancing transition-metal salts or transition-metal complexes such as, for example, Mn, Fe, Co, Ru, or Mo salt complexes or carbonyl complexes. Mn, Fe, Co, Ru, Mo, Ti, V, and Cu complexes having nitrogen-containing tripod ligands, as well as Co, Fe, Cu, and Ru ammine complexes, are also usable as bleach catalysts.

The washing or cleaning agent can contain a thickening agent. The thickening agent can encompass, for example, (meth)acrylic acid (co)polymers, xanthan gum, gellan gum, guar flour, alginate, carrageenan, bentonite, wellan gum, locust bean flour, agar-agar, tragacanth, gum arabic, pectins, polyoses, starch, dextrins, gelatins, and casein.

Suitable acrylic and methacrylic (co)polymers encompass, for example, the high-molecular-weight homopolymers of acrylic acid crosslinked with a polyalkenyl polyether, in particular an allyl ether, of sucrose, pentaerythritol, or propylene (INCI name, according to “International Dictionary of Cosmetic Ingredients” of the Cosmetic, Toiletry and Fragrance Association (CFTA): Carbomer), which are also referred to as carboxyvinyl polymers. Polyacrylic acids of this kind are obtainable from, among others, the 3V Sigma company under the trade name POLYGEL®, e.g. POLYGEL® DA, and from the B.F. Goodrich company under the trade name CARBOPOL®, e.g. CARBOPOL® 940 (molecular weight approx. 4,000,000), CARBOPOL® 941 (molecular weight approx. 1,250,000), or CARBOPOL 934 (molecular weight approx. 3,000,000). Also suitable, for example, are the following acrylic acid copolymers: (i) copolymers of two or more monomers from the group of acrylic acid, methacrylic acid, and their simple esters, formed by preference with $C_{1-4}$ alkanols (INCI: Acrylates Copolymer), included among which are, for example, the copolymers of methacrylic acid, butyl acrylate, and methyl methacrylate (CAS designation according to Chemical Abstracts Service: 25035-69-2), or of butyl acrylate and methyl methacrylate (CAS 25852-37-3), and which are obtainable, for example, from the Rohm & Haas company under the trade names ACULYN® and ACUSOL®, and from the Degussa (Goldschmidt) company under the trade name TEGO® Polymer, e.g. the anionic nonassociative polymers ACULYN® 22, ACULYN® 28, ACULYN® 33 (crosslinked), ACUSOL® 810, ACUSOL® 820, ACUSOL® 823, and ACUSOL® 830 (CAS 25852-37-3); (ii) crosslinked high-molecular-weight acrylic acid copolymers, included among which are, for example, the copolymers, crosslinked with an allyl ether of sucrose or of pentaerythritol, of $C_{10-30}$ alkyl acrylates with one or more monomers from the group of acrylic acid, methacrylic acid, and their simple esters formed preferably with $C_{1-4}$ alkanols Acrylates/$C_{10-30}$ Alkyl Acrylate Crosspolymer), and which are obtainable, for example, from the B.F. Goodrich company under the trade name CARBOPOL®, for example, the hydrophobized CARBOPOL® ETD 2623 and CARBOPOL® 1382 (INCI: Acrylates/$C_{10-30}$ Alkyl Acrylate Crosspolymer), and CARBOPOL® Aqua 30 (formerly CARBOPOL® EX 473). Further suitable polymers are (meth)acrylic acid (co)polymers of the SOKALAN® type (from BASF).

A fatty alcohol is also a suitable thickening agent. Fatty alcohols can be branched or unbranched, and of natural or petrochemical origin. Preferred fatty alcohols have a carbon chain length from 10 to 20 carbon atoms, preferably 12 to 18. It is preferred to use mixtures of different carbon chain lengths, such as tallow fatty alcohol or coconut oil fatty alcohol. Examples are LOROL® Spezial ($C_{12-14}$—ROH) or LOROL® Technisch ($C_{12-18}$—ROH) (both from Cognis).

The washing or cleaning agent can contain 0.01 to 3 wt %, and by preference 0.1 to 1 wt %, thickening agent. The quantity of thickening agent used depends on the type of thickening agent and the desired degree of thickening.

The liquid washing or cleaning agent can also contain an enzyme or a mixture of enzymes. Suitable enzymes are, in particular, those in the classes of hydrolases, such as proteases, (poly)esterases, lipases or lipolytically active enzymes, amylases, cellulases and other glycosyl hydrolases, hemicellulase, cutinases, β-glucanases, oxidases, peroxidases, mannanases, perhydrolases, oxidoreductases, and/or laccases. In the context of the present invention, it is preferable to use proteases, amylases, lipases, cellulases, mannanases, laccases, tannanases, and esterases/polyesterases, as well as mixtures of two or more of these enzymes.

The hydrolases contribute, in the laundry, to the removal of stains such as protein-, fat-, or starch-containing stains, and graying. Cellulases and other glycosyl hydrolases can furthermore contribute to color retention and to enhanced textile softness by removing pilling and microfibrils. Cellobiohydrolases, endoglucanases, and β-glucosidases, which are also called cellobiases, and mixtures thereof, are preferably used as cellulases. Because the different types of cellulase differ in terms of their CMCase and avicelase activities, the desired activities can be adjusted by means of controlled mixtures of the cellulases.

Proteases of the subtilisin type, and in particular proteases obtained from *Bacillus lentus*, are preferably used. Enzyme mixtures, for example of protease and amylase or protease and lipase or lipolytically active enzymes, or protease and cellulase, or of cellulase and lipase or lipolytically active enzymes, or of protease, amylase, and lipase or lipolytically active enzymes, or protease, lipase or lipolytically active enzymes, and cellulase, but in particular protease- and/or lipase-containing mixtures or mixtures with lipolytically active enzymes, are of particular interest in this context. Examples of such lipolytically active enzymes are the known cutinases. The suitable amylases include, in particular, α-amylases, isoamylases, pullulanases, and pectinases.

The quantity of enzyme or enzymes can be 0.01 to 10 wt %, by preference 0.12 to approximately 3 wt %, based on weight of the entire agent. The enzymes are preferably used as liquid enzyme formulation(s). If the washing or cleaning agent contains a mixture of enzymes, then at least one enzyme can be present in granulate form, in encapsulated fashion, or adsorbed onto carrier substances. Very preferred washing or cleaning agents contain cellulase; cellulase and protease; cellulase, protease, and amylase; cellulase, protease, amylase, and lipase or amylase; cellulase, protease, amylase, lipase, and (poly)esterase.

A large number of a very wide variety of salts can be used as electrolytes from the group of the inorganic salts. Preferred cations include the alkali and alkaline earth metals; preferred anions include the halides and sulfates. The proportion of electrolytes in the washing or cleaning agent is usually 0.1 to 5 wt %.

Nonaqueous solvents that can be added to the liquid washing and cleaning agents derive, for example, from the group of the monovalent or polyvalent alcohols, alkanolamines, or glycol ethers, provided they are miscible with water in the indicated concentration range. The solvents are by preference selected from ethanol, n- or isopropanol, butanols, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl, or propyl ether, dipropylene glycol monomethyl or -ethyl ether, diisopropylene glycol monomethyl or -ethyl ether, methoxy-, ethoxy-, or butoxytriglycol, 1-butoxyethoxy-2-propanol, 3-methyl-3-methoxybutanol, propylene glycol t-butyl ether, di-n-octyl ether, and mixtures of these solvents. Nonaqueous solvents can be used in the liquid washing or cleaning agents in quantities between 0.5 and 15 wt %, but preferably below 12 wt % and in particular below 9 wt %.

In order to bring the pH of the washing or cleaning agent into the desired range, the use of pH adjusting agents may be indicated. All known acids and bases are usable here, provided their use is not prohibited for environmental or applications-engineering reasons, or for reasons of consumer safety. The quantity of these adjusting agents usually does not exceed 10 wt % of the entire formulation.

The pH of the washing or cleaning agent is preferably between 4 and 10, and preferably between 5.5 and 8.8.

The liquid washing or cleaning agents can have viscosities in the range of from 100 to 4000 mPas, with values between 300 and 2000 mPas being particularly preferred. The viscosity was determined using a Brookfield LVT-II viscosimeter at 20 rpm and 20° C., spindle 3.

In a preferred embodiment, the washing or cleaning agent can contain one or more perfumes in a quantity of usually up to 15 wt %, by preference 0.01 to 5 wt %, in particular 0.3 to 3 wt % based on total weight of the agent.

Individual odorant compounds, for example, the synthetic products of the ester, ether, aldehyde, ketone, alcohol, and hydrocarbon types, can be used as perfume oils or fragrances. Preferably, however, mixtures of different odorants that together produce an attractive fragrance note are used. Such perfume oils can also contain natural odorant mixtures such as those accessible from plant sources.

In order to improve the aesthetic impression of the washing or cleaning agent, they can be colored with suitable dyes. Preferred dyes, the selection of which should present no difficulty to one skilled in the art, possess excellent shelf stability and insensitivity to other ingredients of the washing or cleaning agents and to light, and no pronounced lasting effects with respect to textile fibers in order not to color them.

Appropriate foam inhibitors that can be used in the washing or cleaning agents are, for example, soaps, paraffins, or silicone compounds, in particular silicone oils, which optionally can be present as emulsions.

Suitable soil-release polymers (which are also referred to as “anti-redeposition agents”) are, for example, nonionic cellulose ethers such as methyl cellulose and methylhydroxypropyl cellulose having a 15 to 30 wt % concentration of methoxy groups and a 1 to 15 wt % concentration of hydroxypropyl groups, based in each case on the nonionic cellulose ethers, as well as the polymers, known from the existing art, of phthalic acid and/or terephthalic acid or their derivatives, in particular polymers of ethylene terephthalates and/or polyethylene and/or polypropylene glycol terephthalates or anionically and/or nonionically modified derivatives thereof. Suitable derivatives encompass the sulfonated derivatives of the phthalic acid and terephthalic acid polymers.

Optical brighteners (so-called “whiteners”) can be added to the washing or cleaning agents in order to eliminate graying and yellowing of the treated textile fabrics. These substances absorb onto the fibers and cause brightening and a simulated bleaching effect by converting invisible ultraviolet radiation into longer-wave visible light, the ultraviolet light absorbed from sunlight being emitted as slightly bluish fluorescence and resulting, with the yellow tone of the grayed or yellowed laundry, in pure white. Suitable compounds derive, for example, from the substance classes of the 4,4'-diamino-2,2'-stilbenedisulfonic acids (flavonic acids), 4,4'-distyrylbiphenyls, methylumbelliferones, cumarins, dihydroquinolinones, 1,3-diarylpyrazolines, naphthalic acid imides, benzoxazole, benzisoxazole, and benzimidazole systems, and pyrene derivatives substituted with heterocycles. The optical brighteners are usually used in quantities of between 0 and 0.3 wt % based on total weight of the finished washing or cleaning agent.

In addition to the graying-inhibiting polysaccharide, the washing or cleaning agent can contain further graying inhibitors. These can encompass size, gelatin, polyvinyl pyrrolidone, or water-soluble polyamides containing acid groups. The quantity of further graying inhibitors is by preference from 0.1 to 5 wt %, based on total weight of washing or cleaning agent.

In order to effectively suppress dye dissolution and/or dye transfer onto other textiles during the washing and/or cleaning of colored textiles, the washing or cleaning agent can contain a color transfer inhibitor. It is preferred that the color transfer inhibitor be a polymer or copolymer of cyclic amines such as vinylpyrrolidone and/or vinylimidazole. Polymers suitable as a color transfer inhibitor encompass polyvinylpyrrolidone (PVP), polyvinylimidazole (PVI), copolymers of vinylpyrrolidone and vinylimidazole (PVP/PVI), polyvinylpyridine-N oxide, poly-N-carboxymethyl-4-vinylpyridium chloride, and mixtures thereof. It is particularly preferred to use polyvinylpyrrolidone (PVP), polyvinylimidazole (PVI), or copolymers of vinylpyrrolidone and vinylimidazole (PVP/PVI) as a color transfer inhibitor. The polyvinylpyrrolidones (PVP) that are used preferably possess an average molecular weight from 2,500 to 400,000, and are available commercially from ISP Chemicals as PVP K 15, PVP K 30, PVP K 60, or PVP K 90, or from BASF as SOKALAN® HP 50 or SOKALAN® HP 53. The copolymers of vinylpyrrolidone and vinylimidazole (PVP/PVI) that are used preferably have a molecular weight in the range from 5000 to 100,000. A PVP/PVI copolymer is available commercially, for example, from BASF under the designation SOKALAN® HP 56.

The quantity of color transfer inhibitor, based on total quantity of the washing or cleaning agent, is preferably from 0.01 to 2 wt %, by preference from 0.05 to 1 wt %, and more preferably from 0.1 to 0.5 wt %.

Alternatively, enzymatic systems encompassing a peroxidase and hydrogen peroxide or a substance yielding hydrogen peroxide in water, can be used as a color transfer inhibitor. The addition of a mediator compound for the peroxidase, for example, an acetosyringone, a phenol derivative, or a phenothiazine or phenoxazine, is preferred in this case. The aforementioned polymeric color transfer inhibitors can also be used additionally.

Because textile fabrics, in particular, those made of rayon, viscose, cotton, and mixtures thereof, can tend to wrinkle due to the individual fibers being sensitive to bending, kinking, pressing, and squeezing perpendicularly to the fiber direction, the washing or cleaning agents can contain synthetic wrinkle-protection agents. These include, for example, synthetic products based on fatty acids, fatty acid esters, fatty acid amides, fatty acid alkylol esters, or fatty acid alkylolamides, or fatty alcohols that are usually reacted with ethylene oxide, or products based on lecithin or modified phosphoric acid esters.

In order to counteract microorganisms, the washing or cleaning agents can contain antimicrobial active substances. A distinction is made here, depending on the antimicrobial spectrum and mechanism of action, between bacteriostatics and bactericides, fungistatics and fungicides, etc. Important substances from these groups are, for example, benzalkonium chlorides, alkylarylsulfonates, halogen phenols, and phenol mercuric acetate; these compounds can also be entirely omitted from the washing or cleaning agents according to the present invention.

The washing or cleaning agents according to the present invention can contain preservatives, preferably those that possess little or no skin-sensitizing potential being used. Examples include sorbic acid and its salts, benzoic acid and its salts, salicylic acid and its salts, phenoxyethanol, formic acid and its salts, 3-iodo-2-propynylbutyl carbamate, sodium N-(hydroxymethyl)glycinate, biphenyl-2-ol, and mixtures thereof. Further suitable preservatives are represented by isothiazolones, mixtures of isothiazolones, and mixtures of isothiazolones with other compounds, for example tetramethylolglycouril.

The washing or cleaning agents can contain antioxidants in order to prevent undesired changes, caused by the action of oxygen and other oxidative processes, to the washing or cleaning agents and/or to the treated textile fabrics. This class of compounds includes, for example, substituted phenols, hydroquinones, catechols, and aromatic amines, as well as organic sulfides, polysulfides, dithiocarbamates, phosphites, phosphonates, and vitamin E.

Increased wearing comfort can result from the additional use of antistatic agents that are additionally added to the washing or cleaning agents. Antistatic agents increase the surface conductivity and thus make possible improved dissipation of charges that have formed. External antistatic agents are usually substances having at least one hydrophilic molecule ligand, and yield a more or less hygroscopic film on the surfaces. These usually surface-active antistatic agents can be subdivided into nitrogen-containing (amines, amides, quaternary ammonium compounds), phosphorus-containing (phosphoric acid esters), and sulfur-containing (alkylsulfonates, alkyl sulfates) antistatic agents. Lauryl- (or stearyl-) dimethylbenzylammonium chlorides are suitable as antistatic agents for textiles or as an additive to washing or cleaning agents, an avivage effect additionally being achieved.

In order to improve the rewettability of the treated textile fabrics and to facilitate ironing of the treated textile fabrics, silicone derivatives can be used in the washing or cleaning agents. These additionally improve the rinsing behavior of the washing or cleaning agents due to their foam-inhibiting properties. Preferred silicone derivatives are, for example, polydialkyl- or alkylarylsiloxanes in which the alkyl groups have one to five carbon atoms and are entirely or partly fluorinated. Preferred silicones include the polydimethylsiloxanes, which optionally can be derivatized and are then aminofunctional or quaternized or have Si—OH, Si—H, and/or Si—Cl bonds. The viscosities of the preferred silicones can be in the range between 100 and 100,000 mPas at 25° C.; the silicones can be used in quantities between 0.2 and 5 wt % based on the entire weight of washing or cleaning agent.

Lastly, the washing or cleaning agents can also contain UV absorbers, which are absorbed onto the treated textile fabrics and improve the light-fastness of the fibers. Compounds that exhibit these desired properties are, for example, compounds that act by radiationless deactivation, and derivatives of benzophenone having substituents in the 2- and/or 4-position. Also suitable are substituted benzotriazoles, acrylates phenyl-substituted in the 3-position (cinnamic acid derivatives) optionally having cyano groups in the 2-position, salicylates, organic Ni complexes, and natural substances such as umbelliferone and endogenous urocanic acid.

Substances that complex heavy metals can be used in order to avoid the heavy-metal-catalyzed breakdown of certain washing-agent ingredients. Suitable heavy metal complexing agents are, for example, the alkali salts of ethylenediaminetetraacetic acid (EDTA) or of nitrilotriacetic acid (NTA), methylglycinediacetic acid sodium salt (MGDA), as well as alkali-metal salts of anionic polyelectrolytes such as polymaleates and polysulfonates.

A preferred class of complexing agents is the phosphonates, which can be contained in the washing or cleaning agent in quantities from 0.01 to 2.5 wt %, by preference 0.02 to 2 wt %, and in particular from 0.03 to 1.5 wt %. Included among these preferred compounds are, in particular, organophosphonates such as 1-hydroxyethane-1,1-diphosphonic acid (HEDP), aminotri(methylenephosphonic acid) (ATMP), diethylenetriamine penta(methylenephosphonic acid) (DTPMP or DETPMP), and 2-phosphonobutane-1,2,4-tricarboxylic acid (PBS-AM), which are usually used in the form of their ammonium or alkali-metal salts. Alternative complexing agents that can be used in the washing or cleaning agent include iminodisuccinates (IDS) or ethylenediamine-N,N'-disuccinate (EDDS).

Washing or cleaning agents according to the present invention can be used to wash and/or clean textile fabrics.

The washing or cleaning agent is manufactured using common and known methods and processes. For example, the constituents of the washing or cleaning agents can be simply mixed in agitator vessels, the water, nonaqueous solvent, and surfactants usefully being prepared first. The fatty acid, if present, is then added, and saponification of the fatty acid component occurs at 50 to 60° C. The further constituents, including the graying-inhibiting polysaccharide, are then added, preferably in portions.

Table 1 below shows the compositions of a washing or cleaning agent E1 according to the present invention.

TABLE 1

Washing or Cleaning Agent E1 Composition

| E1 | Wt % |
|---|---|
| $C_{12-18}$ fatty acid, Na salt | 7 |
| Polyacrylate thickener | 1.5 |
| $C_{12-18}$ fatty alcohol with 7 EO | 12 |
| Sodium lauryl ether sulfate with 2 EO, Na salt | 5 |
| Linear $C_{10-13}$ alkylbenzenesulfonic acid, Na salt | 10 |
| Citric acid, Na salt | 2.5 |
| Phosphonic acid, Na salt | 1 |
| Boric acid, Na salt | 1 |

TABLE 1-continued

| Washing or Cleaning Agent E1 Composition | |
|---|---|
| E1 | Wt % |
| Carboxymethyl cellulose, Na salt (diam. 10-75 nm) | 2 |
| Optical brightener | 0.08 |
| 1,2-Propanediol | 5 |
| Silicone defoamer | 0.15 |
| Cellulase | 0.08 |
| Protease | 1.2 |
| Amylase | 0.5 |
| Perfume | 1.5 |
| Dye | + |
| Water | to make 100 |

The washing or cleaning agent E1 exhibited considerably better graying inhibition compared with a washing or cleaning agent containing sodium carboxymethyl cellulose having an average particle size of 0.5 mm; this is presumably attributable to the greater surface area of the polysaccharide particles. In addition, the washing or cleaning agent E1 was considerably more aesthetically appealing than the comparison washing or cleaning agent, and was shelf-stable.

Although the present invention has been described in detail, it is to be clearly understood that the same is by way of illustration and example only, and is not to be taken as a limitation. The spirit and scope of the present invention are to be limited only by the terms of any claims presented hereafter.

We claim:

1. Washing or cleaning agent comprising one or more surfactants and a graying-inhibiting polysaccharide having a particle size smaller than 100 nm.

2. Washing or cleaning agent according to claim 1 wherein the polysaccharide has a particle size smaller than 50 nm.

3. The washing or cleaning agent according to claim 1 wherein the amount of polysaccharide in the agent is from 0.001 to 10 wt %, based on total weight of the agent.

4. Washing or cleaning agent according to claim 1, wherein the polysaccharide is chosen from carboxymethyl cellulose (CMC), ethersulfonic acid salts of starch, ethersulfonic acid salts of cellulose, acid sulfuric acid ester salts of cellulose, acid sulfuric acid ester salts of starch, methyl cellulose, ethyl cellulose, hydroxyethyl cellulose, hydroxypropyl cellulose, methylhydroxyethyl cellulose, methylcarboxymethyl cellulose, ethylhydroxyethyl cellulose, and mixtures thereof.

5. The washing or cleaning agent according to claim 4 wherein the polysaccharide is carboxymethyl cellulose.

6. The washing or cleaning agent according to claim 5 wherein the polysaccharide is sodium carboxymethyl cellulose.

7. The washing or cleaning agent according to claim 1 wherein the polysaccharide having a particle size smaller than 100 nm has been obtained by applying a mechanical comminution method to larger polysaccharide particles.

8. Method for manufacturing a liquid washing or cleaning agent having one or more surfactants and a graying-inhibiting polysaccharide having a particle size smaller than 100 nm comprising the steps of:

a) processing polysaccharide particles having a particle size larger than or equal to 100 nm by mechanical comminution into polysaccharide particles having a particle diameter smaller than 100 nm; and b) mixing the polysaccharide particles having a particle diameter smaller than 100 nm with the one or more surfactants.

9. The method for manufacturing a liquid washing or cleaning agent according to claim 8, wherein a milling method is used as a mechanical comminution method.

* * * * *